United States Patent [19]
Lester

[11] Patent Number: 5,928,198
[45] Date of Patent: Jul. 27, 1999

[54] MEDICAL TUBE ASSEMBLIES

[75] Inventor: Graham George Lester, Hythe, United Kingdom

[73] Assignee: Smiths Industries Public Limited Company, London, United Kingdom

[21] Appl. No.: 08/908,310

[22] Filed: Aug. 7, 1997

[30]     Foreign Application Priority Data

Aug. 21, 1996 [GB] United Kingdom ................... 9617545

[51] Int. Cl.⁶ .................................................. A61M 5/178
[52] U.S. Cl. .................... 604/164; 604/264; 128/207.14; 128/200.26
[58] Field of Search ......................... 128/207.15, 207.14, 128/200.26, 264, 265, 164, 165; 604/264, 265, 164, 165

[56]                References Cited

U.S. PATENT DOCUMENTS

| | | |
|---|---|---|
| 3,693,624 | 9/1972 | Shiley et al. . |
| 3,774,606 | 11/1973 | Norton .................................... 604/164 |
| 4,798,591 | 1/1989 | Okada . |
| 5,067,496 | 11/1991 | Eisele . |
| 5,186,712 | 2/1993 | Kelso et al. ............................ 604/165 |
| 5,222,487 | 6/1993 | Carr et al. . |
| 5,259,377 | 11/1993 | Schroeder ............................ 128/207.14 |
| 5,390,669 | 2/1995 | Stuart et al. ......................... 128/207.14 |
| 5,460,176 | 10/1995 | Frigger . |
| 5,515,844 | 5/1996 | Chrisopher .......................... 128/200.26 |
| 5,540,662 | 7/1996 | Nicholson ................................ 604/110 |
| 5,546,937 | 8/1996 | Stuart et al. . |
| 5,762,638 | 6/1998 | Shikani et al. ........................... 605/265 |

FOREIGN PATENT DOCUMENTS

| | | |
|---|---|---|
| 0169704 | 1/1986 | European Pat. Off. . |
| 0231634A2 | 8/1987 | European Pat. Off. . |
| 2161709 | 1/1986 | United Kingdom . |
| 95/16485 | 6/1995 | WIPO . |
| 95/20419 | 8/1995 | WIPO . |

*Primary Examiner*—Wynn Wood Coggins
*Assistant Examiner*—Deborah Blyveis
*Attorney, Agent, or Firm*—Pollock, Vande Sande & Amernick

[57]                ABSTRACT

A tracheostomy assembly comprises a tracheostomy tube having an obturator inserted therein, the obturator including two resilient catches at its machine end extending along the outside of a coupling on the machine end of the tracheostomy tube and engaging lips on the coupling. This prevents the obturator being displaced rearwardly. The obturator can be disengaged from the tube by twisting it relative to the tube.

5 Claims, 2 Drawing Sheets

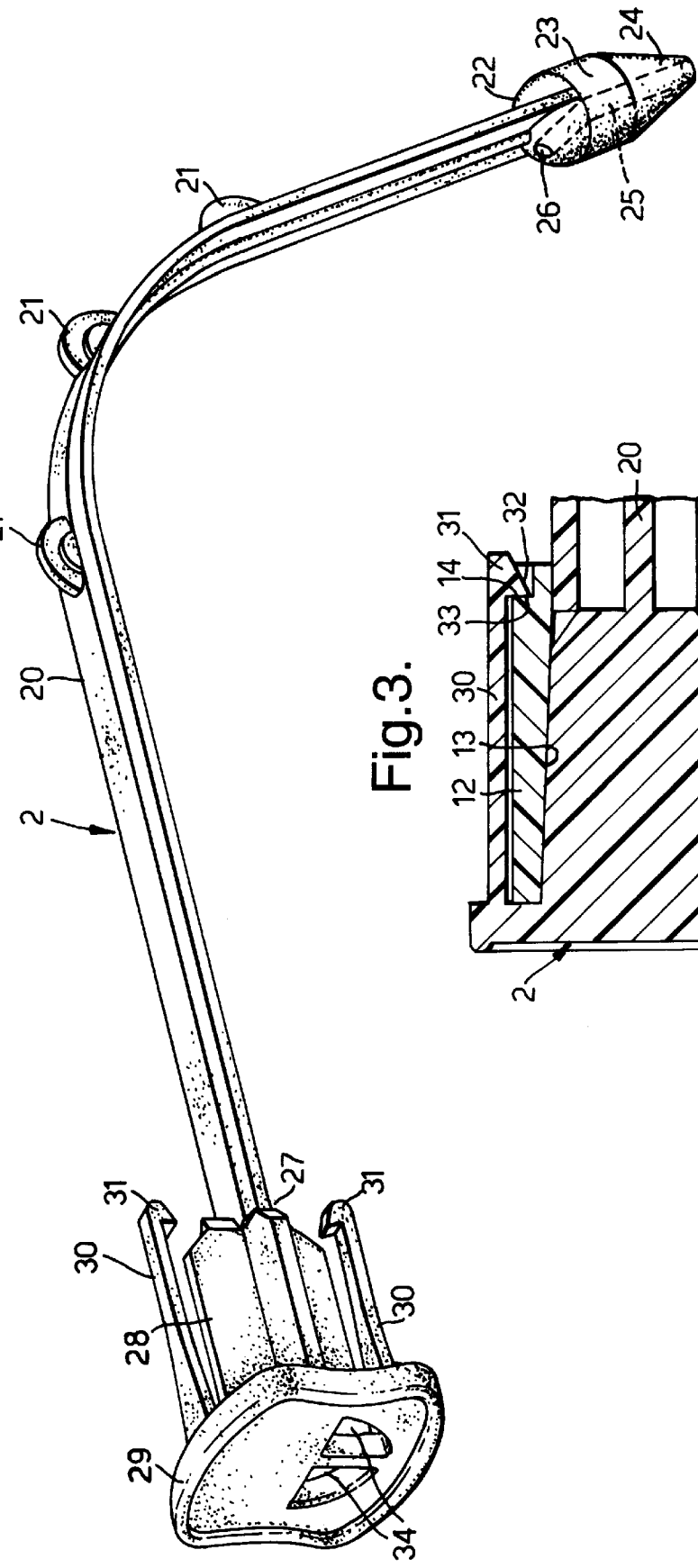

MEDICAL TUBE ASSEMBLIES

BACKGROUND OF THE INVENTION

This invention relates to medical tube assemblies.

The invention is more particularly concerned with medical tube assemblies of the kind including an outer tube and an obturator inserted within the tube.

Tracheostomy tubes are often inserted with the aid of an obturator having a pointed end projecting from the patient end of the tracheostomy tube. The tip of the obturator helps separate tissue, enabling smooth entry of the tube. The obturator also helps stiffen the tube and prevents ingress of tissue into the tube, which could cause blockage. Examples of tracheostomy obturators are described in U.S. Pat. No. 4,246,897, U.S. Pat. No. 5,222,487 and GB2224213. The obturator is pushed into the tracheal tube to its full extent, as limited by a flange abutting the patient end connector on the tracheal tube. The surgeon has to grip the machine end of the obturator and the tube in order to hold the obturator in place and prevent it being pushed rearwardly out of the tube during insertion. Any displacement of the obturator from its correct position may make insertion of the tube more difficult and, by reducing the smoothness of the patient end of the assembly, may cause trauma to tissue around the stoma. After insertion, the obturator is pulled out of the machine end of the tube. Obturators are also used to help insertion of other medical tubes.

BRIEF SUMMARY OF THE INVENTION

It is an object of the present invention to provide an improved medical tube assembly.

According to one aspect of the present invention there is provided a medical tube assembly comprising a medical tube and an obturator inserted within the tube, the obturator having a patient end projecting from the patient end of the tube to aid insertion of the assembly, the obturator and tube being provided at their machine ends with cooperating surface formations arranged, when engaged, to prevent rearward displacement of the obturator relative to the tube.

The cooperating surface formations are preferably arranged such that they can be disengaged by twisting the obturator through a small angle relative to the tube. The cooperating surface formations may be provided by a resilient catch and a lip. The obturator preferably has two resilient catches extending along opposite sides of the tube and engaging respective lips on the tube. The tube may have a coupling at its patient end, the surface formation on the obturator being provided by at least one resilient catch that extends along the outside of the coupling and engages a surface formation on the coupling. The obturator may have a strap of rectangular section extending between its machine end and its patient end. The patient and machine ends of the obturator both preferably have an air passage therethrough. The obturator may be molded from a plastics material.

According to another aspect of the present invention there is provided a tracheostomy tube assembly comprising a tracheostomy tube and an obturator inserted within the tube, the obturator having a pointed patient end projecting from the patient end of the tube to aid insertion of the assembly, the obturator and tube being provided at their machine ends with cooperating surface formations arranged, when engaged, to prevent rearward displacement of the obturator relative to the tube, and said tube and obturator together providing an air passage extending along the assembly to enable the patient to breath while the assembly is being inserted.

A tracheostomy tube assembly according to the present invention, will now be described, by way of example, with reference to the accompanying drawings.

BRIEF DESCRIPTION OF THE DRAWINGS

FIG. 2 is a perspective view of the obturator of the assembly; and

FIG. 3 is a cross sectional side elevation of the machine end of the assembly.

DETAILED DESCRIPTION OF THE PREFERRED EMBODIMENT

Figure 1:
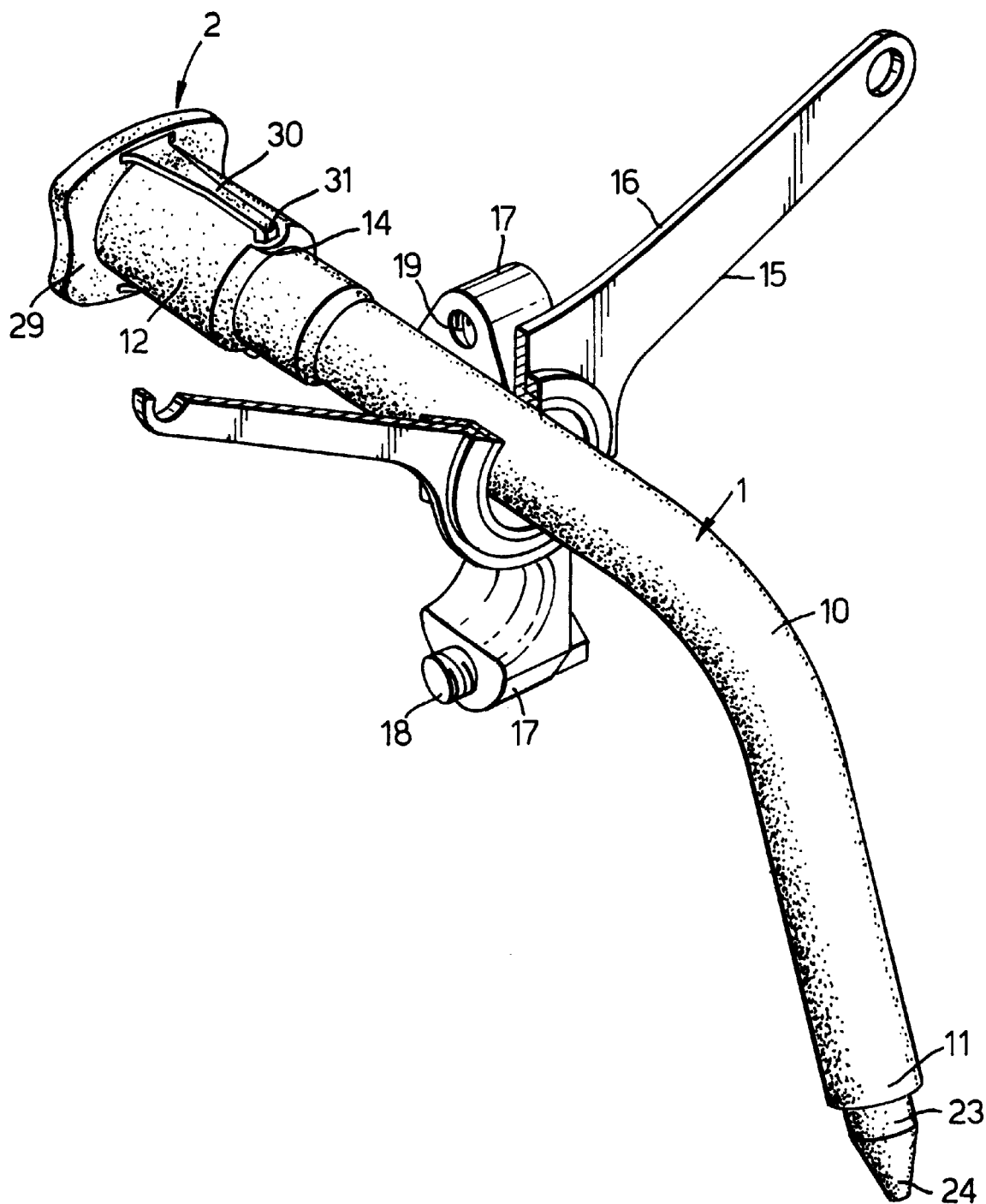
FIG. 1 is a partly cut-away perspective view of the assembly.

The assembly comprises a tracheostomy tube 1 and an obturator 2.

The tube 1 has a conventional shaft 10 of circular section, which is curved or bent to suit the anatomical requirements of the patient. The patient end 11 of the shaft 10 is cut square and rounded to be atraumatic. At its machine end, the shaft 10 is bonded to a coupling 12 having a female tapered bore 13 shaped to receive a male tapered coupling (not shown) connected to a patient ventilation or anaesthetic circuit. Alternatively, where the patient is breathing spontaneously, the coupling 12 is left open. Externally, the coupling 12 is of cylindrical shape apart from surface formations provided by two, short undercut lips 14 located diametrically opposite one another at the patient end of the coupling. The tube 1 also includes a conventional, adjustable flange 15 of the kind described in GB2227941. The flange 15 has a flexible plate 16 to which two semi-circular arms 17 are attached and hinged with one another. The arms 17 can be clamped together, to lock the flange 15 at any location along the shaft 10, by means of a bolt 18 on one arm that engages a threaded aperture 19 on the other arm. The shaft 10 has an inflatable cuff (not shown) towards its patient end, for sealing with the inside of the trachea; alternative tubes need not include such a cuff.

The obturator 2 is molded from a stiff but bendable, resilient plastics material and has a strap 20 of generally rectangular shape extending along the major part of its length, the width of the strap being slightly less than the internal diameter of the shaft 10 of the tube 1. The strap 20 is bent at right angles, to the same shape as that of the shaft 10, and has three semicircular projections 21 on its convex side, in the region of the bend, so that the strap is held substantially centrally within the tube 1 in the region of the bend. At its patient end 22, the obturator is provided with a bullet shape nose 23, which is a close fit within the patient end 11 of the tube 1. The nose 23 has a pointed tip 24, which, in use, projects from the tube 1 so as to form a pointed continuation of the patient end of the shaft 10. A bore 25 extends along the nose 23 from its tip 24 to an opening 26 at its rear end.

At its machine end 27, the obturator 2 has an enlarged, cruciform section 28 with a tapered exterior, which is a close friction fit within the coupling 12 of the tube 1. A flange 29 extends radially at the machine end of the cruciform section 28 and provides a grip by which the obturator 2 can be inserted and removed from the tube 1. Two resilient arms 30 extend forwardly from the flange 29 on opposite sides of the obturator 2. The arms 30 are terminated at their patient end by surface formations in the form of inwardly-directed catches 31 formed by an inclined ramp 32 and a ledge 33. The dimensions of the arms 30 are such that, when the flange 29 abuts the machine end of the coupling 12, the arms extend along opposite sides of the coupling 12 with the catches 31 engaging under the lips 14, thereby preventing the obturator 2 being removed from the tube. Two vent holes 34 are formed through the flange 29 in alignment with the corners between the cruciform section 28.

In use, the obturator 2 is pushed fully into the tube 1 so that the nose 23 projects from the patient end 11 of the tube and so that the catches 31 engage the lips 14 on the coupling 12. The flexible nature of the strap 20 enables it to be bent during insertion and removal to conform to the shape of the tube 1, without deforming the tube itself. The assembly is inserted in the usual way, the obturator 2 providing a tapered lead into the tracheostomy for the tube 1. Rearward movement of the obturator 2 relative to the tube 1 is prevented by engagement of the catches 31 with the lips 14. The patient can breath through the assembly during insertion because of the bore 25 through the nose, the passage between the strap 20 of the obturator 2 and the inside of the tube, and the holes 34 in the flange 29. When the assembly has been inserted to the correct location, the obturator 2 is removed by gripping the flange 29 and twisting it through about 20° so that the catches 31 come out of alignment with the lips 14 and can be pulled rearwardly along the outside of the coupling 12. After removal of the obturator 2, the coupling 12 can be connected to a ventilation circuit or left open, in the usual way.

The present invention makes insertion of the assembly easier because there is no need to hold the machine end of the obturator. Also, there is no risk of the obturator being displaced rearwardly during insertion, thereby ensuring that damage to the tissue around the stoma is minimized. The provision of the lips on the coupling, at the machine end of the tube do not prevent the tube being connected to conventional couplings. It will be appreciated that the obturator could be locked with the tube against rearward displacement by alternative surface formations on the machine end of the obturator and tube. The invention could be used with tubes, other than tracheal tubes, where it is necessary to prevent displacement of an obturator relative to a tube.

What I claim is:

1. A medical tube assembly comprising: a medical tube having a patient end and a machine end, said machine having a coupling with an open end and two lips on opposite sides of the coupling towards an opposite end of said coupling; and a plastics, molded obturator inserted within said tube, said obturator having a patient end and a machine end, said patient end of said obturator projecting from said patient end of said tube to aid insertion of said assembly, said obturator having two elongate resilient catches molded integrally with the obturator, the catches extending longitudinally substantially the length of said coupling along an exterior of the coupling, each of said catches engaging a respective one of said lips such that rearward displacement of said obturator relative to said tube is prevented and such that the catches can be released from said lips by twisting the obturator through a small angle relative to said tube.

2. A medical tube assembly according to claim 1, wherein said obturator is molded from a plastics material.

3. A tracheostomy tube assembly comprising: a tracheostomy tube having a patient end and a machine end coupling; and an obturator inserted within said tube, said obturator having a machine end and a pointed patient end projecting from the said patient end of said tube to aid insertion of said assembly, said obturator having two elongate resilient catches molded integrally with the obturator, the catches extending longitudinally substantially the length of said coupling along opposite external sides of the coupling, each of said catches engaging said coupling towards a patient end of the coupling such that rearward displacement of said obturator relative to said tube is prevented and such that the catches can be released by twisting the obturator through a small angle relative to said tube, and said tube and said obturator together providing an air passage extending along said assembly to enable a patient to breath while said assembly is being inserted.

4. A medical tube assembly comprising: a medical tube having a patient end and a machine end; and an obturator inserted within said tube, said obturator having a patient end and a machine end, said patient end of said obturator projecting from said patient end of said tube to aid insertion of said assembly, said obturator having a strap of rectangular section extending between said machine end and said patient end of the obturator, and said obturator and said tube being provided at their machine ends with cooperating surface formations arranged, when engaged, to prevent rearward displacement of said obturator relative to said tube.

5. A medical tube assembly according to claim 4, wherein said patient and machine ends of said obturator both have an air passage therethrough.

* * * * *